(12) United States Patent
Amberg et al.

(10) Patent No.: US 8,429,230 B2
(45) Date of Patent: Apr. 23, 2013

(54) METHOD FOR TRANSMITTING A COMMUNICATION INVITATION RELATING TO A MEDICAL DICOM IMAGE

(75) Inventors: Jessica Amberg, Bubenreuth (DE); Per Anselm Mahr, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 233 days.

(21) Appl. No.: 12/786,797

(22) Filed: May 25, 2010

(65) Prior Publication Data

US 2010/0306328 A1 Dec. 2, 2010

(30) Foreign Application Priority Data

May 26, 2009 (DE) .......................... 10 2009 022 681

(51) Int. Cl.
*G06F 15/16* (2006.01)
*G06K 9/40* (2006.01)

(52) U.S. Cl.
USPC ............ 709/205; 382/128; 382/173; 709/206

(58) Field of Classification Search .................. 705/3, 2; 709/203, 227, 238, 205, 206; 726/3; 370/389, 370/352; 382/254, 128, 173
See application file for complete search history.

(56) References Cited

U.S. PATENT DOCUMENTS

| | | | |
|---|---|---|---|
| 2002/0038381 A1* | 3/2002 | Gendron et al. | 709/238 |
| 2006/0184676 A1* | 8/2006 | Tanimoto | 709/227 |
| 2006/0224665 A1* | 10/2006 | Takahashi et al. | 709/203 |
| 2007/0189266 A1* | 8/2007 | Izumi et al. | 370/352 |
| 2007/0192138 A1* | 8/2007 | Saito et al. | 705/3 |
| 2007/0192140 A1* | 8/2007 | Gropper | 705/3 |
| 2008/0013534 A1* | 1/2008 | Tsuzuki et al. | 370/389 |
| 2009/0319291 A1* | 12/2009 | Noordvyk et al. | 705/2 |
| 2010/0100935 A1* | 4/2010 | Sato et al. | 726/3 |
| 2010/0191541 A1* | 7/2010 | Prokoski | 705/2 |
| 2011/0225003 A1* | 9/2011 | McCallie | 705/2 |

* cited by examiner

*Primary Examiner* — Jungwon Chang

(57) ABSTRACT

A method for transmitting an invitation to a communication relating to a medical image in a DICOM data record from a person who has access to the image to a partner is proposed. The invitation is stored as information in the DICOM data record of the image. The DICOM data record is transmitted to a server. With reference to the invitation, the server determines a message channel which leads to the partner. The server transmits the invitation to the partner via the message channel.

5 Claims, 2 Drawing Sheets

METHOD FOR TRANSMITTING A COMMUNICATION INVITATION RELATING TO A MEDICAL DICOM IMAGE

CROSS REFERENCE TO RELATED APPLICATIONS

This application claims priority of German application No. 10 2009 022 681.8 filed May 26, 2009, which is incorporated by reference herein in its entirety.

FIELD OF THE INVENTION

The invention relates to a method for transmitting an invitation to a communication relating to a medical image in DICOM format from a person having access to the image to a partner.

BACKGROUND OF THE INVENTION

Users such as e.g. doctors or medical assistants, and medical imaging systems such as e.g. X-ray or MR equipment, often work in conjunction with additional electronic systems. One such system is a PACS (Picture Archiving and Communication System), for example. This is used to electronically store the medical image data that has been generated, e.g. X-ray recordings, MR image data records or reconstruction images. The image data is stored in the standard DICOM (Digital Imaging and Communications in Medicine) format here. In this context, a DICOM data record or DICOM image contains the actual medical image and its associated header data. Said header data is broken down into various standard tags and free or private tags. The standard tags of the DICOM header contain e.g. information concerning the means used to generate the image, the image type, and the recording parameters used to generate the image.

A person dealing with the image sometimes needs or desires a communication with a partner, e.g. a colleague from another specialist area, with regard to the image. The staff member concerned will usually then attempt to contact an appropriate partner, e.g. in the corresponding specialist discipline, e.g. by telephone. If the partner can be reached by telephone, for example, said partner must view the pictures either locally, i.e. at the location of the person, or on a networked PACS station at the current location of the partner, or on a remote server which is connected via Web-PACS, for example. A problem arises here in that DICOM systems are closed systems which generally work without e-mail support. Simply sending the image via e-mail (particularly during an operation or intervention) is therefore impossible. Furthermore, a recipient of the DICOM image would not be able readily to open or view the image, but would need a special DICOM viewer for this purpose.

A further problem arises if the person desiring the communication is a doctor who is currently working under sterile conditions at an operating table. With the exception of the sterile operating module that has been prepared for them, this person cannot actually use any other devices, e.g. a non-sterile telephone, in order to communicate with the partner. In such cases, it is currently normal practice for e.g. an operating room nurse to hold a non-sterile telephone to the ear of the doctor, so that the doctor does not have to touch it.

SUMMARY OF THE INVENTION

The present invention addresses the problem of providing an improved method for transmitting an invitation to a communication relating to an image in DICOM format from a person to a partner.

The problem is solved by a method according to the claims. A person has access to a medical image which is present in DICOM format. In other words, the person is currently occupied with, examining, evaluating or using this image. The person would like (generally as soon as possible) to conduct a communication with a partner in relation to the image, and therefore would like to invite the partner to the corresponding communication. The inventive method serves to transmit this invitation to the partner. According to the invention, the invitation is stored as information in the DICOM data of the image. The image or DICOM data is then transmitted to a server. The server evaluates the invitation and, with reference to the invitation, determines a suitable message channel which leads to the partner. Finally, the server transmits the invitation to the partner via the message channel.

The invention is based on the idea of providing the DICOM image or the DICOM data record with a specific DICOM tag which reflects the information relating to the invitation to the communication. This tag triggers a predefinable response at the storage location, i.e. in the server, and consequently on a suitable communication medium forming the message channel to the partner. These responses deliver the invitation to the partner. In other words, the tag therefore links a person, a partner and a DICOM image data record to a specified task, namely the communication concerned.

Since all of the communication management runs via the server, the addressed partner in the required specialist discipline does not individually or personally have to search on the DICOM server, by name or other criteria such as patient ID, for the image that is to be the subject of the communication. By virtue of the method according to the invention, said paltrier is automatically sent the image, or information that has been automatically generated in relation to it, e.g. via a work list or an e-mail.

As a result of transferring the communication steps onto the server, neither the person nor the partner, for example, is obliged to remain continuously on the telephone until e.g. corresponding patient images are found by the partner from the required department.

By virtue of the invention, existing technologies are extended and/or combined. According to the invention, one or more additional "communication DICOM tags" are used or inserted in a DICOM data record. The invention makes use of various mechanisms from knowledge management portals: "Urgent calls" allow a plurality of people to be notified, in order to reach a person in this group of people as quickly as possible. "Predefined user groups" bring people who are suitable for a specific task together into a group, from which at least one partner can then knowledgeably enter into communication. "Communities of practice" are practice-related communities of people who are informally connected to each other and deal with similar tasks. Corresponding messages or communication invitations are therefore classified by being assigned to one of the structures cited above.

Transactions in the method can be Web-based and executed in the form of Web services. These can also be integrated into "Singapore", for example, this being a software platform developed by Siemens to provide client-server communication. In this case, the platform associates the DICOM tag information with further information that is available from the medical information environment, e.g. a hospital IT system. The communication can be automated in this way, e.g. as an option using the Singapore server or an existing communication facility, e.g. a Siemens HICOM telephone system.

Depending on the configuration of the communication requirements, the invention allows notification of e.g. only those doctors present on site or only those doctors currently logged onto a console. According to the invention, it is also possible to distinguish between different levels of urgency in relation to the communication requirements.

The invention has the advantage of increasing the probability of reaching, and/or of reducing the time required to reach a partner for the purpose of communication, particularly in urgent cases. Time-intensive manual searching for contact information and/or countless manual attempts to reach a suitable partner are no longer necessary. In very urgent cases, it is therefore possible simply to send an alarm from the server via a correspondingly networked IT system to "all" relevant people, for example, in order to ensure that at least one partner answers immediately.

In this context, the server can always be a networked server or a "standalone" system.

If the message channel is suitable not only for transmitting the communication invitation to the partner, but also for allowing the transfer of the image in the form of the complete DICOM data record, an advantageous embodiment of the method provides for the server also to transmit the DICOM data record to the partner. The partner can then become familiar with the DICOM image already before entering onto the communication with the person, e.g. studying it as appropriate and consequently entering into the requested communication in a state of readiness.

In a further advantageous embodiment of the method, with reference to the invitation, the server obtains additional information which is correlated to the invitation from information sources that are networked to the server. The server makes the additional information available to the person and/or the partner. In other words, the server analyzes the invitation and links additional information to the image, said additional information being helpful to the desired communication. In other words, the server thus links various information sources which are relevant to a complete workflow in relation to the communication or to solving the problem that must currently be communicated. For example, the server can provide blood values, a patient history of the patient, or similar, in addition to the image data, if this information could be relevant in the communication.

In a further advantageous embodiment, the server determines the message channel with reference to a resource management system that is networked to the server. In this context, the invention makes use of the realization that time recording, materials management and other resource management systems or control systems are used today in the majority of medical facilities, e.g. hospitals. This will increase further in the future. In addition, telephones and pagers are a widely used communication medium in the environment concerned. As a result of the server accessing all of these media and/or information, a suitable message channel to the partner can be found easily, e.g. the current location of the partner, including a valid telephone number, e-mail address or similar, at which the partner can be currently be reached.

According to the invention, it is therefore possible to select e.g. a partner who is currently on duty or who matches the specialist discipline required for the communication. This partner can therefore be notified directly and personally by the server, e.g. depending on duty schedules. Corresponding message channels can be e.g. SMS, e-mail, pager or an automatically generated telephone call.

In a further variant of the method, the person is therefore a first person and the partner is a second person in a group of people. The first person does not explicitly specify the communication partner in the form of a name, for example, but merely submits a request to the effect that said first person wishes to speak to one—whichever one—of the available radiologists as a group of people. On the basis of the invitation, the server then selects an actual second person from the group of people and transmits the invitation to the actual second person concerned.

As a result of storing the invitation in the DICOM header of the image, the image information of any desired type is then marked as e.g. "to be reviewed", i.e. requiring further examination. With reference to attendance information for various people from corresponding specialist areas, this being known in the hospital management system, the server can then automatically determine and notify the correct i.e. suitably knowledgeable partners.

In a further embodiment of the method, the server checks whether the partner shows a response to the invitation within a time period, e.g. enters into communication with the person. In the absence of a response, the server determines an alternative partner and transmits the invitation to this partner. In the case of the above cited group of people, for example, a third person is therefore selected from the group of people if the second person does not reply to the first person quickly enough with regard to the communication.

In this context, it is possible to provide for e.g. "urgent calls" to all people in a relevant group of people. As soon as one person enters into the communication, e.g. the others are notified that their invitation to the communication is now invalid.

If the partner accepts the invitation, i.e. if the person receives a communicated second opinion, a return call or similar, the information relating to the completed communication can also be forwarded to a workflow management system. This then initiates the next predefined step, e.g. in an operational sequence if the person is a doctor performing the operation. The corresponding information relating to a response or resolution of the communication can in turn be stored as information in the DICOM data of the image, e.g. by adding a new tag.

In a further embodiment of the method, the person sends the invitation while performing a medical procedure under sterile conditions on a patient associated with the image. For a person working under sterile conditions, the use of such communication media, which are not available in sterile form in the operating room, is resource-intensive or unfeasible. By virtue of the inventive method, the conventional handling of DICOM images is used, and the doctor therefore proceeds in the customary manner, since doctors can already manage the DICOM image data today on correspondingly sterile operator devices.

BRIEF DESCRIPTION OF THE DRAWINGS

For a further description of the invention, reference is made to the exemplary embodiments from the drawings in which, using a schematic diagram in each case.

DETAILED DESCRIPTION OF THE INVENTION

Figure 1:
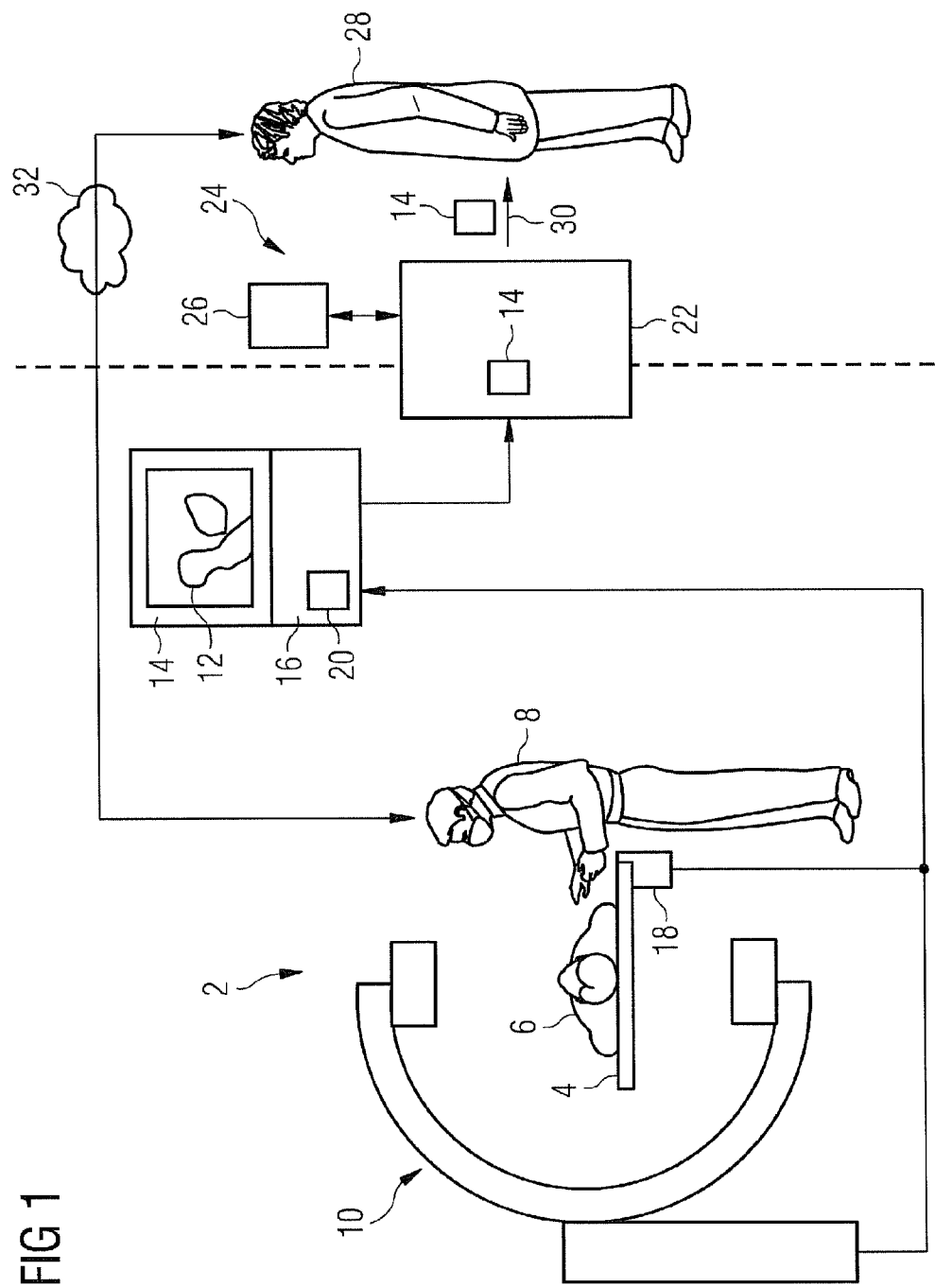
FIG. 1 shows a medical work station at which the inventive method is carried out.

FIG. 1 shows a medical work station 2 featuring a patient couch 4, on which a patient 6 is operated by a person 8, specifically a doctor in the sterile environment in the exemplary embodiment. The work station 2 comprises an X-ray C-arm 10, which is used to record an image 12 of the patient 6. The image 12 is part of a DICOM data record 14, which additionally contains a DICOM header 16.

The person 8 examines the image 12 and comes to the conclusion that consultation with a colleague is necessary in this case. For the purpose of controlling the imaging functionality, an operating module 18 which can be operated in a sterile manner is attached to the couch 4. The person 8 therefore selects, in a sterile manner, at the operating module 18 which is likewise embodied in a sterile manner, a function "forward image/images/data record to specialist discipline xyz for the purpose of feedback/review/second opinion". In other words, by activating the corresponding function, the person 8 requests a communication with a partner from the corresponding specialist discipline xyz.

The imaging system (C-arm 10 in this example) then first provides the data record 14 or the DICOM header 16 with an additional DICOM tag which corresponds to the invitation 20 to the communication. According to the invention, the invitation 20 contains both the specialist discipline xyz and the request for feedback, including the telephone number of the treatment room in which the work station 2 is located.

The C-arm 10 sends the data record 14 to a server 22 via DICOM-Send. The server 22 checks the data record 14 (i.e. the DICOM data) and recognizes that it contains the invitation 20 and that the image 12 must be forwarded as quickly as possible to the specialist discipline xyz for assessment.

The server 22 is networked to a management system 24, which contains information relating to all staff in all specialist disciplines, including their communication data. With reference to a duty schedule 26 which is stored in the management system 24, the server 22 determines a partner 28 of the specialist discipline xyz and forwards the data record 14 to the partner 28. It uses the message channel 30 for this purpose, said channel being a broadband Internet connection in the example. The partner 28 receives the data record 14, appraises it, and establishes a connection to the person 8 via the specified telephone number in the form of a communication 32, in order to discuss the data record 14.

In an alternative embodiment, the partner 28 is not currently at a networked work station. The message channel 30 is therefore a pager or telephone channel. The server 22 then notifies the partner 28 via pager or an automatic telephone call, optionally with redialing or an alternative telephone number if the first telephone number is occupied. The partner 28 can then initially enter into a telephone connection with the person 8 in order to conduct the communication 32. If necessary, the partner 28 can then proceed to a location at which the data record 14 can be received from the server 22 for further appraisal.

Figure 2:
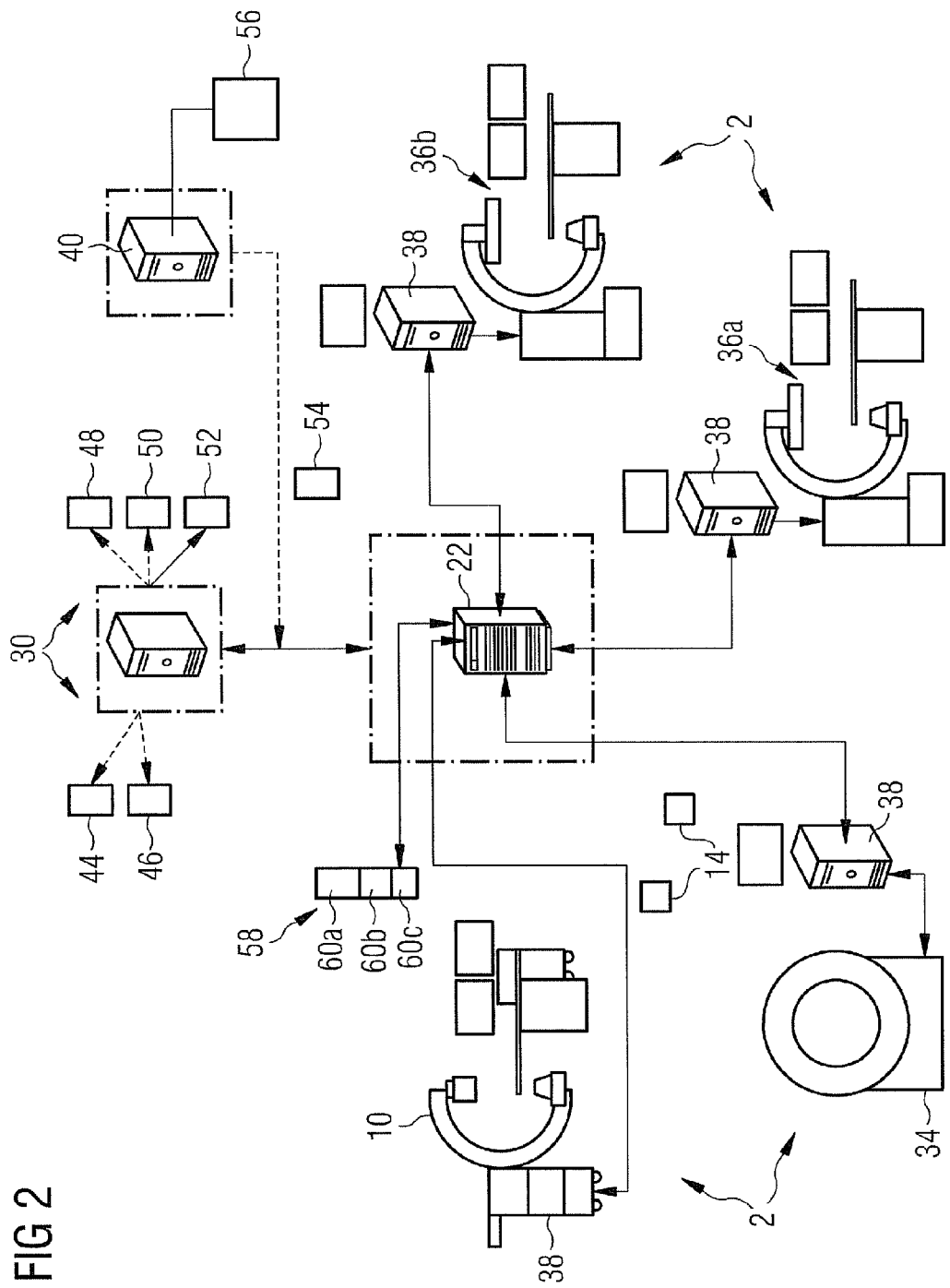
FIG. 2 shows a network structure comprising a plurality of medical work stations.

FIG. 2 shows a network structure, e.g. in a hospital in which a plurality of medical work stations 2 are networked. The server 22, i.e. the data server, triggers various responses due to a DICOM tag. A plurality of work stations 22 are attached to the server 22, specifically a mobile C-arm 10, a computer tomograph 34 and two angiography systems 36a,b in the example. Each of the work stations 2 has an imaging system 38, and each imaging system exchanges the generated DICOM image data with the server 22 in the form of data records 14. The server 22 is additionally connected to a HIS 40 (hospital information system), which manages patient data, employee data, duty schedules, contact data, etc.

With reference to the invitation 20, the server 22 consults the HIS 40 for the contact data of the partner 28 and thus determines a suitable message channel 30.

In an alternative embodiment, with reference to the invitation 20, the server 22 also obtains additional information 54 from an information source 56. This is e.g. a medical database which is attached to the HIS 40. The information 54 is therefore medical background knowledge relating to the diagnosis of the patient 6, said diagnosis being stored in the DICOM data record 14. The server 22 transmits the information 54 to the person 8 and the partner 28.

For the purpose of conducting the communication between the person 8 and the partner 28, the server 22 is also connected to a communication server 42, which preferably offers access to all currently available communication channels. In the example, these comprise an Internet-based telephone VoIP 44 (Voice over Internet Protocol), a mobile radio channel GSM 46, an interface for e-mail 48, a pager 50 and a telephone 52.

In a further embodiment, the invitation does not specify a physical person, but merely seeks a "radiologist". The group 58 of radiologists includes a plurality of radiologists 60a-c. With reference to the duty schedule from the HIS 40, the server now selects the radiologist 60b, since this radiologist is currently on duty and is logged on to an imaging system 38.

List of Reference Signs
2 Work station
4 Couch
6 Patient
8 Person
10 C-arm
12 Image
14 Data record
16 Header
18 Operating module
20 Invitation
22 Server
24 Management system
26 Duty schedule
28 Partner
30 Messaging channel
32 Communication
34 Computer tomograph
36a,b Angiography system
38 Imaging system
40 HIS
42 Communication server
44 VoIP
46 GSM
48 E-mail
50 Pager
52 Telephone
54 Information
56 Information source
58 Group
60a-c Radiologists

The invention claimed is:

1. A method for transmitting an invitation for a communication relating to a medical image in a DICOM data record from a person who has access to the image to a partner, comprising:
providing the DICOM data record with a specific communication DICOM tag comprising information relating to the invitation, wherein the specific communication DICOM tag comprises a specialist discipline of the partner and a request for feedback;
storing the invitation in the DICOM data record of the image;
transmitting the DICOM data record to a server;
selecting the partner who matches the specialist discipline by the server;
determining a message channel which leads to the partner by the server;

transmitting the invitation to the partner via the message channel by the server;
checking whether the partner shows a response to the invitation within a time period by the server;
determining an alternative partner in an absence of a response by the server; and
transmitting the invitation to the alternative partner by the server,
wherein the server analyzes the invitation and obtains additional information relating to the invitation from an information source networked to the server and makes the additional information available to the person and/or the partner.

2. The method as claimed in claim 1, wherein the server transmits the DICOM data record to the partner.

3. The method as claimed in claim 1, wherein the server determines the message channel with reference to a resource management system to which the server is networked.

4. The method as claimed in claim 1, wherein the person is a first person and the partner is a second person in a group of people and wherein:
the server determines the second person from the group of people with reference to the invitation, and
the server transmits the invitation to the second person.

5. The method as claimed in claim 1, wherein the person sends the invitation while performing a medical procedure under sterile conditions on a patient associated with the image.

* * * * *